United States Patent [19]

Baxter et al.

[11] 4,350,764

[45] Sep. 21, 1982

[54] MICROBIOLOGICAL SYNTHESIS OF BETA ENDORPHIN

[75] Inventors: John D. Baxter; Ivy Fettes, both of San Francisco, Calif.; John Shine, Curtin, Australia

[73] Assignee: The Regents of the University of California, Berkeley, Calif.

[21] Appl. No.: 128,711

[22] Filed: Mar. 10, 1980

[51] Int. Cl.$^3$ .................... C12P 21/02; C12N 15/00; C12N 1/20; C12N 1/00

[52] U.S. Cl. ................................. 435/69; 435/68; 435/70; 435/172; 435/253; 435/317; 435/820; 435/848; 435/849; 260/112.5 R

[58] Field of Search ............... 260/112.5; 435/68, 69, 435/71, 172, 207, 253, 317, 820, 848, 849

[56] References Cited

U.S. PATENT DOCUMENTS

4,038,222  7/1977  Li ............................................ 260/8
4,237,224 12/1980  Cohen et al. ........................... 435/68

OTHER PUBLICATIONS

Roberts et al., *Proc. Nat. Acad. Sci.*, vol. 74, (1977), pp. 4826–4830.
Mains, et al., *J. Biol. Chem.*, vol. 251, (1976), pp. 4115–4120.
Nakanishi et al., *Proc. Nat. Acad. Sci.*, vol. 73, (1976), pp. 4319–4323.
Roberts et al., *Biochem.*, vol. 17, (1978), pp. 3609–3619.
Eipper et al., *J. Biol. Chem.*, vol. 253, (1978), pp. 5732–5744.
Li et al., *Biochem. Biophys. Res. Comm.*, vol. 71, (1976), pp. 19–25.
Roberts et al., *Proc. Nat. Acad. Sci.*, vol. 76, (1979), pp. 2153–2157.
Nakanishi, et al., *Nature*, vol. 278, (1979), pp. 423–427.
Polisky, et al., *Proc. Nat. Acad. Sci.*, vol. 73, (1976), pp. 3900–3904.
Itakura, et al., *Science*, vol. 198, (1977), pp. 1056–1063.
Martial, et al., *Science*, vol. 205, (1979), pp. 602–606.
Dixon, et al., *Biochem. J.*, vol. 109, (1968), pp. 312–314.
Li. et al., *Proc. Nat. Acad. Sci.*, vol. 76, (1979), pp. 3276–3278.
Seeburg, et al., *Nature*, vol. 276, (1978), pp. 795–798.
Seeburg, et al., *Nature*, vol. 270, (1977), pp. 486–494.
Shine, et al., *Nature*, vol. 270, (1977), pp. 494–499.
Bolivar, et al., *Gene*, vol. 2, (1977), pp. 95–113.
Scheller, et al., *Science*, vol. 196, (1977), pp. 177–180.
Maxam, et al., *Proc. Nat. Acad. Sci.*, vol. 74, (1977), pp. 560–564.
Laemmli, *Nature*, vol. 227, (1970), pp. 680–685.
Rees, et al., *Endocrinology*, vol. 87, (1971), pp. 254–261.
Allen et al., *Proc. Nat. Acad. Sci.*, vol. 75, (1978), pp. 4972–4976.
Hunter, et al., *Nature*, vol. 194, (1962), pp. 495–496.
Klee, et al., *Proc. Nat. Acad. Sci.*, vol. 71, (1974), pp. 3474–3477.
Hamprecht, et al., *Hoppe-Seylers' Z. Physiol. Chem.*, vol. 354, (1973), pp. 1633–1641.
Traber, et al., *Nature*, vol. 253, (1975), pp. 120–122.
Dulbecco, *Virology*, vol. 8, (1959), pp. 396–397.
White, et al., *Annl. Biochem.*, vol. 85, (1978), pp. 451–460.
Itakura et al., *J. Am. Chem. Soc.*, vol. 97 (1975), pp. 7327–7332.
Zubay, *Ann Rev. Genetics*, vol. 7, (1973), pp. 267–287.

*Primary Examiner*—Thomas G. Wiseman
*Attorney, Agent, or Firm*—Keil & Witherspoon

[57] ABSTRACT

DNA comprising the naturally occurring nucleotide sequence coding for amino acids 44-90 of β-lipotropin and including the entire coding region for β-endorphin with the exception of the C-terminal glutamine was modified, transferred to an expression transfer vector, and expressed as a fusion protein. The fusion protein was further modified in vitro to yield mature β-endorphin. β-endorphin was purified from a bacterial lysate. The structure and biological activity of the resulting product was proven by immunological assay, and by two independent assays designed to demonstrate biological activity.

11 Claims, 5 Drawing Figures

MICROBIOLOGICAL SYNTHESIS OF BETA ENDORPHIN

This invention was made with Government Support under grant no. AM-18878-04 awarded by the department of Health and Human Services. The Government has certain rights in this invention.

BACKGROUND AND PRIOR ART

Figure 1:
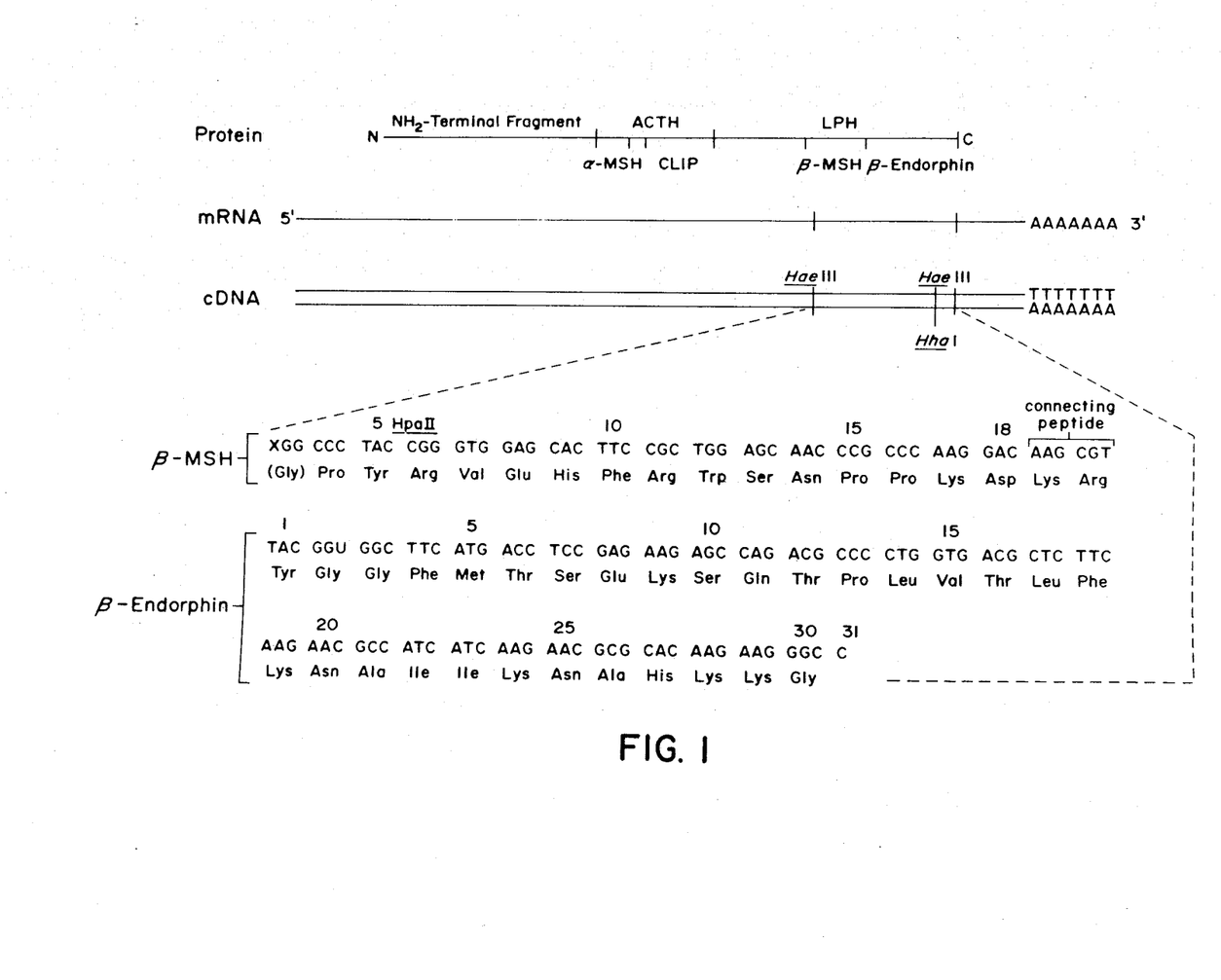

In the mid-1970's, it was discovered that opium alkaloids such as morphine and heroin bind to specific receptors in brain and other tissues. The specific binding reaction was found to be prerequisite to the production of the characteristic biological effects of analgesia and euphoria for which the opiates are well known. The findings led to the discovery of endogenous substances which also bind to the opiate receptors. These naturally occurring compounds are termed endorphins, for endogenous morphine-like substances. A number of such compounds have been isolated and characterized and shown to be peptides having similarities in their amino acid sequence. The most active of these substances is β-endorphin, a polypeptide of 31 amino acids whose sequence (except for the c-terminal gistamine) is shown in FIG. 1.

In the mammalian pituitary, β-endorphin is synthesized as a precursor protein of molecular weight about 30,000. The precursor protein includes the amino acid sequences of adrenocorticotropic hormone (ACTH), β-lipotropin (β-LPH), α-melanocyte stimulating hormone (α-MSH), β-melanocyte stimulating hormone (β-MSH), corticotrophin-like intermediate lobe peptide (CLIP), met-enkephalin and β-endorphin. (See, e.g. Roberts, J. L. and Herbert, E., *Proc. Natl. Acad. Sci.* U.S. 74, 4826 (1977); Mains, E. and Eipper, B. A., *J. Biol. Chem.* 251, 4115 (1976); Nakanishi, S., et al., *Proc. Natl. Acad. Sci.* 73, 4319 (1976)). Normally, the precursor protein is processed by post-translational proteolysis and glycosylation, to generate the individual peptide hormones (Roberts, J. L., et al., *Biochemistry* 17, 3609 (1978); Eipper, B. A. and Mains, R. E., *J. Biol. Chem.* 253, 5732 (1978)).

To the extent the functions of the hormonal peptides contained within the precursor protein sequence are understood, they appear to be related generally to physical and biochemical adaptations to stress. The physiological responses to β-endorphin appear to be analogous to the physiological effects of such opium alkaloids as morphine and heroin. Such effects are well known and include analgesia, altered emotional state, and reduced anxiety.

The medical uses of β-endorphin are generally those for which the opiate alkaloids are presently employed. Therefore, the availability of an endogenous substance capable of producing the same effects is highly attractive to the medical profession. In addition, the expansion of medical uses for the opiates coupled with world population increase will lead to a projected world-wide shortage of morphine and its analogs within a few years. At the present time, β-endorphin is known to be useful as an analgesic and in the treatment of intractable pain. Intra-cerebral administration of β-endorphin, via an implanted delivery tube, has been employed in the successful treatment of such forms of intractable pain as phantom limb pain. In addition, β-endorphin is effective as an intravenously administered analgesic. β-endorphin has been reported to be effective in the treatment of certain mental disorders related to mood, affect and anxiety, including schizophrenia. It is also known that β-endorphin binds to the opiate receptors in the gut so that it can be applied in the treatment of such gastrointestinal disorders as severe diarrhea, which presently are treated with opiates. It has also been shown that the administration of β-endorphin induces increased plasma levels of prolactin and may therefore prove effective as a long-term birth control agent. Because of the presently known and predicted uses for β-endorphin in medical care, there is presently a substantial market for the compound as an investigational drug. Prior to the present invention, the compound was obtainable in small quantity and great expense either by purification from brain extracts or by chemical synthesis. At current prices, the market for β-endorphin as an investigational drug in the United State alone is estimated at several million dollars per year. Clearly, a method for producing β-endorphin in quantity, with substantial economies of scale, is highly desirable. The present invention provides such a method.

Although β-endorphin can be obtained from extracts of brain tissue, the yields are relatively small. Chemical synthesis has been achieved by Li, C.H., et al., *Biochem. Biophys. Res. Commun.* 71, 19 (1976). DNA sequences coding for all or part of the ACTH/β-endorphin precursor protein have been cloned by the cDNA method (Roberts, J. L., et al., *Proc. Natl. Acad. Sci.* 76, 2153 (1979); Nakanishi, S., et al., *Nature* 278, 423 (1979)). The cloning of a DNA coding for a portion of the ACTH/β-endorphin precursor protein is described in application Ser. No. 972,430, now U.S. Pat. No. 4,322,499, incorporated herein by reference. The genetic material cloned therein was employed as a starting material in the present invention.

Methods for the expression of heterologous DNA in a microorganism are now known. In principle, the heterologous DNA coding sequence is inserted in a DNA transfer vector at a point located within an expressible operon. The inserted sequence must be in reading frame phase with the coding sequence of the peron, and oriented in the same direction with respect to translation. When the conditions are met, translation of the operon results in "readthrough" to the inserted coding sequence such that the protein produced is a fusion protein comprising an N-terminal amino acid sequence coded by the expressible operon, followed by an amino acid sequence coded by the insert. See Polisky, B., et al, *Proc. Natl. Acad. Sci.*, 73, 3900 (1976); Itakura, K., et al, *Science*, 198, 1056 (1977). Several expressible operons have been employed, including insertion in the β-galactosidase gene, the β-lactamase gene, and the tryptophan operon.

Although the genetic code is said to be "universal" in the sense that all known living organisms use the same code, it is well known that higher organisms, such as mammals, preferentially employ a set of codons which differs from that preferred by microorganisms such as bacteria. This observation has led investigators to choose synthetic coating sequences employing codons preferred by bacteria. Such a strategy does not appear to be necessary, at least for the expression of immunologically cross-reactive material, since both synthetic and naturally occurring sequences can be expressed in bacteria to yield an immunologically active product (Itakura, K., et al., *Science* 198, 1056 (1977); Material, J. A., et al., *Science* 205, 602 (1979)). Until the present invention, however, evidence of a biologically functional hormone has not been presented, either for synthetic or naturally occurring coding sequences. The present invention demonstrates the feasibility of using coding sequences comprising naturally occurring mammalian codons to achieve expression of biologically active protein by a recombinant microorganism.

SUMMARY OF THE INVENTION

The present invention is believed to provide the first instance of the synthesis of a mammalian hormone by a microorganism transformed by a coding sequence comprising naturally occurring mammalian codons, wherein the biological activity of the product was demonstrated. The invention is exemplified by the bacterial synthesis of mouse β-endorphin. The mouse endorphin differs from human endorphin merely by two amino acids and the mouse endorphin is thought to be biologically active in humans.

The microbiological synthesis of β-endorphin is accomplished in the present invention by modifying an existing cloned coding sequence, expressing the modified coding sequence as a fusion protein in a microorganism, modifying the fusion protein to specifically remove the non-endorphin portion of the fusion protein, yielding the β-endorphin sequence per se, purifying β-endorphin from a bacterial lysate and proving the identity of the purified material by immunological reactivity and by specific tests of biological function.

Abbreviations used herein are as follows:

| | |
|---|---|
| A = Adenine | dATP = deoxyadenosine triphosphate |
| G = Guanine | dGTP = deoxyguanosine triphosphate |
| C = Cytosine | dCTP = deoxycytosine triphosphate |
| T = Thymine | dTTP = thymidine triphosphate |

(DNA base sequences are written as single strands with the indicated polarity, e.g. 5'-ATGC-3'. When both strands are shown, the lower strand has the opposite polarity. It will be understood that deoxynucleosides are intended in all DNA sequences).

| | |
|---|---|
| Ala = Alanine | Leu = Leucine |
| Met = Methionine | Ile = Isoleucine |
| Ser = Serine | Val = Valine |
| Gly = Glycine | Lys = Lysine |
| Cys = Cysteine | Arg = Arginine |
| Glu = Glutamic acid | Phe = Phenylalanine |
| Asp = Aspartic acid | Tyr = Tyrosine |
| Gln = Glutamine | Trp = Tryptophan |
| Asn = Asparagine | His = Histidine |
| Thr = Threonine | Pro = Proline |

Amino acid sequences are written from the $NH_2$-terminal end on the left to the COOH-terminal end on the right.

HEPES = N-2-hydroxyethylpiperatine-N'-2-ethanesulfonic acid
EDTA = Ethylenediaminetetracetic acid
Tris = Hydroxymethyl aminomethane (base) or hydroxymethyl aminomethanehydrochloride (acid)
SDS = Sodium dodecyl sulfate
β-gal = β-galactosidase

DETAILED DESCRIPTION OF THE INVENTION

The cloned coding sequence used as the starting point in the present invention contained the coding information for amino acids 44–90 of the beta lipotropin portion of the ACTH/β-endorphin precursor protein. A map of the precursor protein and detailed structure of a portion of the cloned coding sequence are shown in FIG. 1. The sequence codes for all of β-endorphin except the C-terminal glutamine. The strategy of the present invention involves insertion of the mammalian coding sequence into an internal position in a bacterial gene such that the cloned mammalian sequence is in phase with the bacterial coding sequence. It is thus necessary to modify the cloned mammalian sequence fragment in order to re-create the codon for the carboxy-terminal amino acid, insert a stop codon and link the fragment in phase to a bacterial gene. It is also necessary to devise a method for the release of mature β-endorphin from the fusion protein.

Figure 2:
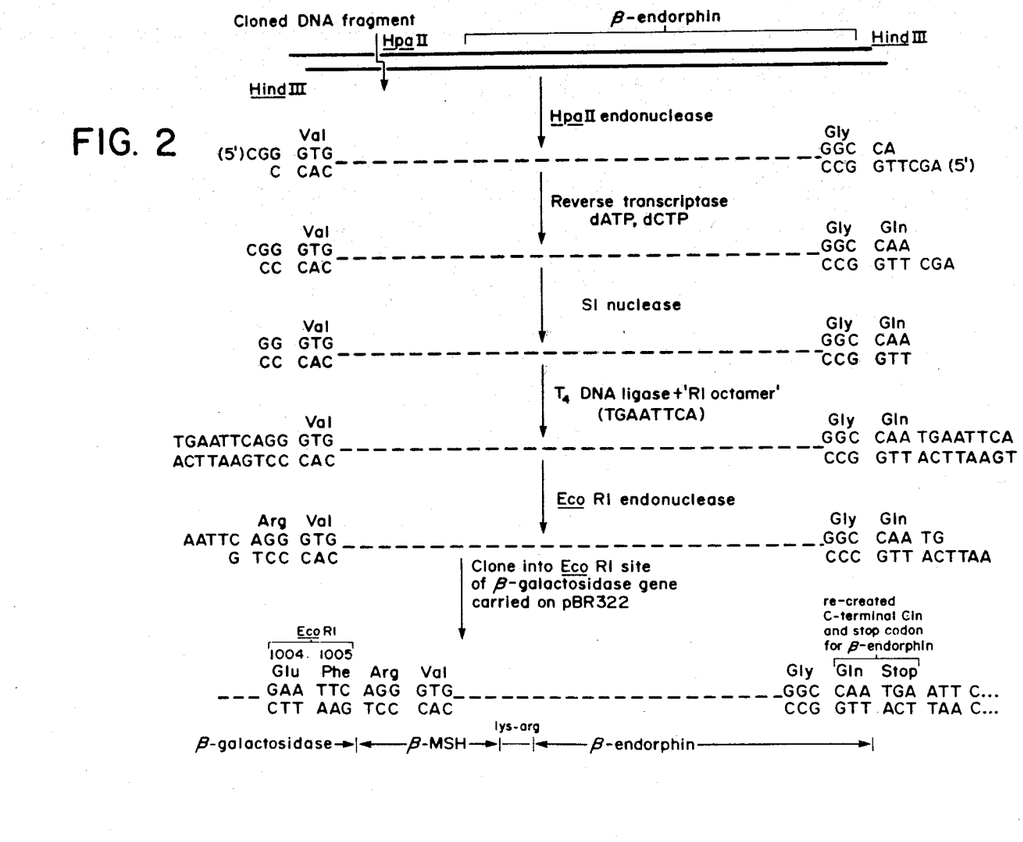

The approach to these problems is outlined in FIG. 2. The cloned mammalian coding fragment was released from the DNA transfer vector in which it was inserted by HindIII endonuclease digestion, since the fragment had been inserted into the transfer vector using HindIII linkers. The released fragment was first cleaved in the β-MSH coding region with HpaII endonuclease in order to facilitate the insertion in phase with respect to reading frame, in the bacterial gene. The single stranded HpaII and HindIII terminate were then partially filled in by a reaction catalysed by reverse transcriptase in the presence of dATP and dCTP. The reaction re-created the 3'-terminal glutamine codon and added a cytosine residue at the HpaII site. The remaining unpaired terminal nucleotides were then removed by S1 nuclease digestion and the blunt-ended fragment connected to a synthetic octanucleotide containing the recognition site for EcoR1, in a DNA-ligase catalysed reaction.

In principle, the cloned mammalian coding sequence fragment could be inserted into a variety of bacterial genes including but not limited to the β-galactosidase gene, the β-lactamase gene, and genes of the tryptophan operon. The partial filling in of unpaired single stranded ends can be employed to advantage in many similar situations. The choice of bacterial gene into which to insert the coding sequence fragment will depend upon the reading frame phase of the insertion site, the availability of suitable restriction sites and desired properties of the resulting fusion protein. The present invention is exemplified by an insertion into the bacterial gene coding for β-galactosidase, at an EcoR1 site which is known to occur at the codon for amino acid 1004 (Itakura, K., et al., Science 198, 1056 (1977)).

The use of the synthetic octanucleotide containing the recognition site for EcoR1 served a dual purpose of providing the EcoR1 terminae necessary for ligation with the β-galactosidase gene and also provided a stop codon immediately following the 3'-terminal glutamine codon. The modified fragment was then inserted into the EcoR1 site of a DNA transfer vector carrying the appropriate bacterial gene. For example, in the present invention, the plasmid pBR322 carrying the lac control region and the coding sequence for β-galactosidase was employed. The plasmid has a single EcoR1 site at the codon for amino acid 1004 of β-galactosidase, and is designated pβgal.

Figure 3:
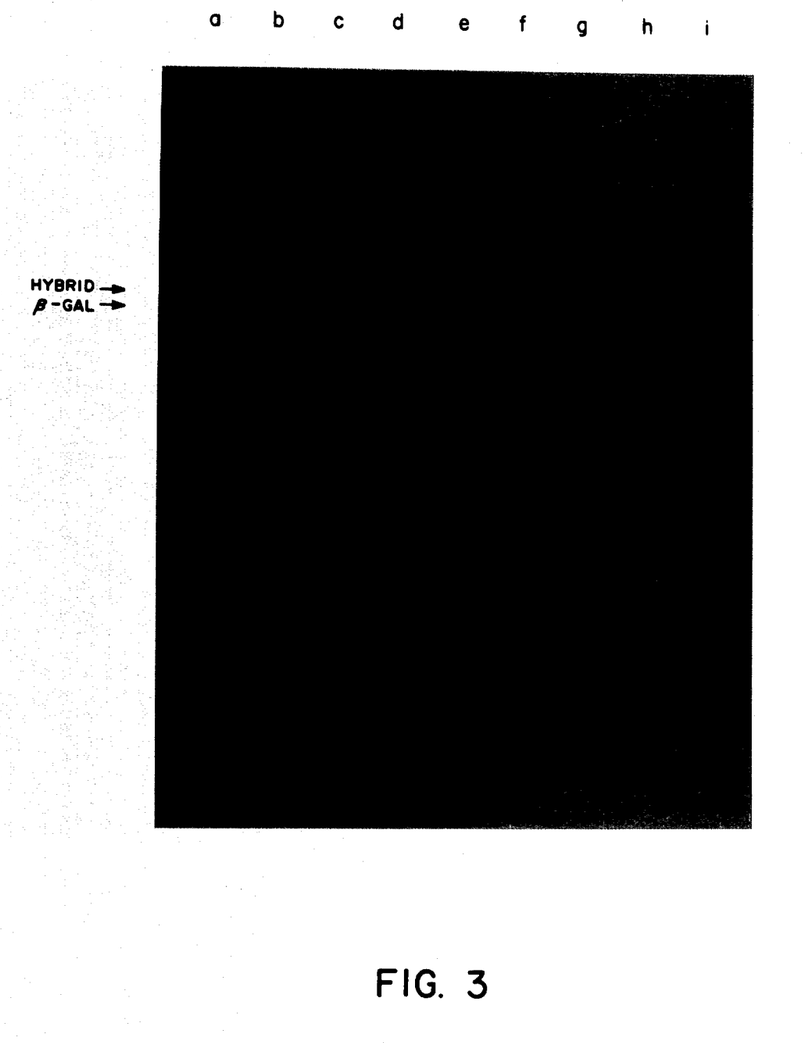

The recombinant plasmid formed by inserting the modified β-endorphin coding sequence at the EcoR1 site designated pβgal-end, was used to transform a culture of the bacteria Escherichia coli. Growth of the transformed cells in culture resulted in the formation of a fusion protein under control of the lac promotor. Synthesis of the fusion protein could be demonstrated by SDS-polyacrylamide gel electrophoresis of cell proteins (FIG. 3). Extracts of cells carrying the plasmid pβgal-end lacked a band in the position expected for the normal β-galactosidase protein, but demonstrated the appearance of a new band reflecting a protein approximately 30 amino acids larger than β-galactosidase, the size expected for the β-galactosidase-β-MSH-β-endorphin fusion protein. It was found that the fusion protein was insoluble and could be recovered from a high-speed pellet of a cell sonicate, where it represented a substantial proportion of the recoverable protein.

Figure 4:
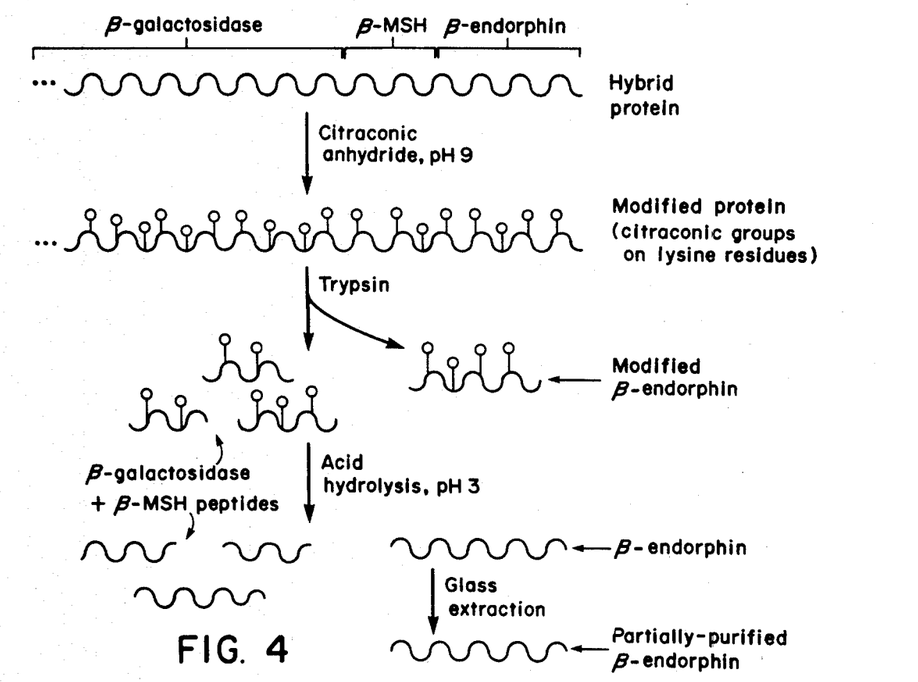

The steps used to release mature β-endorphin from the hybrid protein are shown in FIG. 4. The arginine residue preceding the β-endorphin sequence (FIG. 1) was used as a site for proteolytic cleavage by trypsin. Since β-endorphin contains several internal lysine residues that would be susceptible to trypsin cleavage, it was necessary to specifically protect the lysine residues against trypsin attack. It was discovered that the lysine residues in β-endorphin could be protected from attack by trypsin by prior reaction with citraconic (methylmaleic) anhydride in vitro (Dixon, H. B. F. and Perham, R. N., *Biochem. J.* 109, 312 (1968)). Thus, after dissolving the precipitated fusion protein and treating with citraconic anhydride at pH 9, the β-endorphin (containing the modified lysine groups) was released from the fusion protein by cleavage with trypsin. Native β-endorphin was subsequently produced by removing the citraconic groups at pH 3. The native β-endorphin was then further purified from this preparation as described infra.

The β-endorphin was shown to be immunologically reactive with antiserum raised against mouse endorphin. By quantitative analysis of the results, it was estimated that the bacteria synthesized approximately $8 \times 10^4$ molecules of β-endorphin per cell. The β-endorphin prepared as described was further characterized for biological function in two separate tests. The first test was the ability of the endorphin to bind to opiate receptors from rat brain and to compete in such binding with a known opiate agonist (enkephalinamide) and a known opiate antagonist (naloxone). Endorphin, prepared according to the invention, displaced both the opiate agonist and the opiate antagonist from the rat brain opiate receptors.

In a separate assay, the ability of endorphin, prepared according to the invention, to inhibit the stimulation of adenylate cyclase activity by prostaglandin $E_1$ in a neuroblastomaglioma hybrid cell line was tested. The prostaglandin $E_1$ stimulation is known to be inhibited by morphine and the inhibitory effect of morphine is reversed by naloxone. Endorphin produced according to the invention showed a significant inhibition of prostaglandin $E_1$ stimulation of adenylate cyclase activity, which inhibition was reversed by addition of the opiate antagonist naloxone.

The present invention represents the first known instance of the synthesis of a mammalian hormone by a microorganism, transformed with a coding sequence comprising naturally occurring mammalian codons wherein proof of a functional protein product was adduced. The techniques disclosed herein may be applied to the preparation of peptides that differ from the mouse endorphin demonstrated in the examples. Thus, human endorphin differs from the mouse peptide only at position 27 where a tyrosine residue is present instead of a histidine and at position 31 where a glutamine residue replaces a glutamic acid. The mouse endorphin is known to cross-react immunologically with human endorphin and no difference in biological activity in human cells is known. The β-endorphin expression plasmid described herein may be used as starting material to program bacterial plasmids that direct the synthesis of analogs of β-endorphin which may have altered or selectively different opiate agonist or antagonist activities. In particular, modifications of the C-terminal part of the amino acid sequence are known to profoundly affect biological activity, Li, C.H., et al., *Proc. Natl. Acad. Sci.* 76, 3276 (1979), have shown that $Gly^{--}$-endorphin, $Gly^{--}$-endorphinamide and $Gly^{--}$-endorphinylglycine are more potent opiate agonists than endorphin itself. The present invention provides methods for modifying the naturally occurring sequence, as originally cloned, so that such modified amino acid sequences are expressed. Furthermore, it is anticipated that other feasible modifications within the scope of the invention, will yield endorphin-like peptides that function as opiate antagonists.

The steps in constructing a system for synthesizing β-endorphin using bacteria are next described in detail, with particular reference to the synthesis of mouse endorphin, as described in the following examples.

The characteristic features of the described method are applicable to the synthesis of other endorphins from other species and in particular to the synthesis of human β-endorphin.

EXAMPLE 1

Construction of a Plasmid for the Expression of β-endorphin Sequences by *E. coli*

In the following experiments, digestions with restriction endonucleases were carried out under conditions optimized for each enzyme. Enzymes were obtained commercially (New England BioLabs, Cambridge, Mass.) and optimal reaction conditions according to the supplier's recommendations were employed unless noted otherwise. The use of reverse transcriptase and suitable reaction conditions have been described previously by Seeburg, P. H., et al., *Nature* 276, 795 (1978); Seeburg, P. H., et al., *Nature* 270 486 (1977); and Shine, J., et al., *Nature* 270 494 (1977). Recombinant plasmids were isolated from chloroamphenicol-amplified cultures as previously described by Bolivar, F., et al., *Gene* 2, 95 (1977)).

A mammalian coding sequence of 150 base pairs was obtained from the plasmid pMAE-1 (Roberts, J. L., et al., supra.) by HindIII endonuclease digestion, followed by electrophoresis in a 7% (w/v) polyacrylamide gel. The mammalian DNA coding fragment was then modified by digestion of ~500 ng DNA with five units of HpaII endonuclease at 37° C. for 1 hour in 20 μl of 6 mM Tris pH 7.5, 6 mM $MgCl_2$ and 6 mM β-mercaptoethanol. The reaction mixture was then extracted with phenol and DNA was recovered by ethanol precipitation. The DNA was then redissolved in 50 μl of a reaction mixture containing reverse transcriptase buffer and 500 μM each of dATP and dCTP. The mixture was incubated at 37° with 10 units of reverse transcriptase for 15 minutes. At the end of the reaction, unincorporated triphosphates were removed by chromatography on Sephadex G-50 (TM Pharmacia Inc., Uppsala, Sweden). DNA was recovered by ethanol precipitation. The DNA was then re-dissolved in 50 μl of 0.3 M NaCl, 30 mM Na acetate pH 4.5, 3 mM $ZnCl_2$, incubated with 5 units of $S_1$ nuclease at 20° C. for 5 minutes, then recovered by phenol extraction and Sephadex G-50 chromatography.

The double-stranded blunt-ended DNA was then covalently joined to the synthetic octamer

```
TGAATTCA
ACTTAAGT
```

Heyneker, W. L. et al, *Nature* 263, 748 (1976)). The octamer functions as a linker sequence and contains the restriction site for endonuclease EcoR1. See Scheller, R. H., et al., *Science* 196, 177 (1977). The joining reaction was catalysed by bacteriophage T4DNA ligase (New England BioLabs) in a 40 μl reaction mixture containing 60 mM Tris (pH 7.5), 8 mM MgCl$_2$, 10 mM β-mercaptoethanol, 1 mM ATP, 2 μl of enzyme, ~500 ng DNA and a 20-fold molar excess of synthetic linker. The reaction mixture was incubated for 24 hours at 4° C. After the addition of 0.1 M NaCl and digestion with 50 units of EcoR1 endonuclease at 37° C. for 5 hours, the unreacted linker fragments were removed by Sephadex G-50 chromatography.

The DNA transfer vector chosen for insertion was the plasmid pβgal described supra. The plasmid was digested with EcoR1 endonuclease to convert the circular plasmid DNA to linear DNA having a unique sequence. The linear DNA was further treated with alkaline phosphatase to prevent the subsequent formation of plasmid pβgal in a DNA ligase catalysed reaction, as described in U.S. Pat. No. 4,264,731 incorporated herein by reference. The modified mammalian DNA coding sequence was inserted into the treated pβgal DNA in a DNA ligase catalysed reaction, as described in the references cited at the beginning of this example. Recombinant plasmids were used to transform *E. coli* RR1, Bolivar, F., supra. Single colonies of recombinant transformants were isolated and grown in 3 ml cultures to prepare plasmid DNA therefrom. The mammalian insert contains an asymmetrically located HaeIII site (GGCC) which yields differently sized fragments upon HaeIII endonuclease digestion, depending upon the orientation of the insert. A clone having a correctly inserted mammalian sequence was selected for further analysis. The nucleotide sequence of the inserted DNA was determined by the method of Maxam, A. and Gilbert, W., *Proc. Natl. Acad. Sci.* 74, 560 (1977). The sequence of the modified insert was shown to be identical to that shown in FIG. 2.

EXAMPLE 2

Expression of a β-Galactosidase-β-Endorphin Fusion Protein

*E. coli* RR1 cells harboring either plasmid pβgal-end of pβgal were grown at 37° C. to mid-log phase in L-broth and harvested by centrifugation. The cells were dissolved in SDS sample buffer (Laemmli, U.K., *Nature* 227, 680 (1970)). Protein equivalent to 50 μl of original culture was subjected to electrophoresis in a 7% (w/v) polyacrylamide gel and visualized by staining with coomassie blue. Results are shown in FIG. 3. Lane a shows the protein banding pattern derived from *E. coli* RR1; Lane b shows proteins obtained from *E. coli* RR1 induced with 2 mM isopropyl-β-thiogalactoside (IPTG); Lane c: proteins obtained from *E. coli* RR1 carrying pβgal; Lane d: proteins obtained from *E. Coli* RR1 carrying pβgal and induced with IPTG; Lane e: proteins obtained from *E. coli* RR1 carrying pβgal-end; Lane f: proteins from *E. coli* RR1 carrying pβgal-end induced with IPTG; Lane g: protein obtained from *E. coli* RR1 carrying pβgal-end prepared by harvesting the cells by centrifugation, resuspending the cells in phosphate buffered saline, disrupting the cells by sonication and fractionating the sonicate by centrifugation at 15,000 rpm for 30 minutes and analyzing the supernatant fraction; Lane h: protein from *E. coli* RR1 carrying pβgal-end fractionated as described in Lane g, analyzing the pellet after solubilization in SDS; Lane i: proteins obtained from *E. coli* RR1 carrying pβgal-end after treatment to amplify the plasmid DNA with 50 μg/ml chloramphenicol, followed by 3 hours' growth in fresh L-broth.

The electrophoresis banding pattern of proteins derived from cells transformed with pβgal-end shows substantial amounts of protein not found in non-recombinant cultures and decreased amounts of β-galactosidase. The position of β-galactosidase is shown by arrow #1 and that of the β-galactosidase-β-endorphin fusion protein by arrow #2. When cells are disrupted by sonication, the fusion protein is found associated with the cell pellet. Increased amounts of the fusion protein are formed after induction with IPTG, consistent with the conclusion that expression of the β-galactosidase-β-endorphin fusion protein is under lac operon control *E. coli* RR1 carrying pβgal-end, and the plasmid pβgal-end, were placed on deposite at the American Type Culture Collection, 12301 Parklawn Drive, Rockville, Md. on Mar. 6, 1980. The bacteria has ATCC accession number 31614. The plasmid has ATCC accession number 40024.

EXAMPLE 3

Release of β-endorphin from the Fusion Protein

The sequence of steps detailed in this example is shown diagrammatically in FIG. 4. The pellet fraction, obtained as described in Example 2, from cells bearing pβgal-end, was dissolved in 10 ml of 6 M guanidinium chloride, 1% (v/v) 2-mercaptoethanol and centrifuged at 20,000 rpm for 1 hour. Citraconic anhydride (obtained from Fisher Chemical Company, Santa Clara, Calif.) was added to the supernatant fraction in three lots, 10 μl each, over a 15-minute period, during which time the pH was maintained between 9 and 11 by the addition of 1 N NaOH, as described by Dixon, H. B. F. and Perham, R. N., supra. The reaction mixture was then dialyzed overnight against 50 mM ammonium bicarbonate.

The dialyzed solution was incubated with trypsin (Worthington Biochemical Corporation, Freehold, New Jersey), 0.5 mg/ml, at 37° C. for 12 hours. Trypsin was then inactivated by addition of phenylmethylsulfonyl fluoride (PMSF) to 1 mM for a 1-hour additional incubation period. The protein was deprotected by the addition of formic acid to 1% (v/v) and lyophilised. The dried protein was re-dissolved in Tris buffer pH 7.6 to yield a final protein concentration of 0.5-1.0 μg/μl. The foregoing preparation was used for some of the immunological and biological activity tests.

This procedure has general utility for cleavage of a leader of prepeptide sequence, since such sequences are often found to be joined by a lys-arg connection to the active peptide. The procedure will also be effective in cases where internal arginine residues exist in the active peptide, since those arginines will often be protected by the folded configuration of the peptide.

EXAMPLE 4

Purification of β-endorphin

Further purification of β-endorphin was accomplished by a modification of the technique devised for extraction and purification of ACTH by Rees, L. H. et al., *Endocrinology* 87, 254 (1971). To 0.5 ml aliquots of the endorphin preparation described in Example 3, were added 0.5 ml of horse serum (Grand Island Biological Company, Santa Clara, Calif.) and 50 mg glass powder, 140 mesh (Corning Glass Works Leached Silica Glass, Code no. 7930, Corning, N.Y., water washed to remove fines and oven dried 24 hours at 120° C.) in a 15 ml plastic centrifuge tube. These samples were vortexed for 30 seconds and then centrifuged for 5 minutes at 2,000 rpm. The supernatant was discarded and the glass adsorbant was washed with 3 ml of water. The endorphin was removed from the glass by adding 1 ml of 50% (v/v) acetone in 0.25–0.5 N HCl, vortexing for 30 seconds and then centrifuging as described. The supernatant was then transferred to polystyrene tubes and evaporated to dryness with a fine stream of nitrogen in a water bath at 45° C. Dried samples were re-dissolved in Tris buffer pH 7.6.

EXAMPLE 5

Immunological Activity

Immunological activity of β-endorphin produced according to the present invention was measured by its ability to compete with radioactively labeled human β-endorphin for antiserum directed against mouse β-endorphin. The human hormone differs from that of mouse only at position 27, where a tyrosine is present instead of a histidine residue. This change does not inhibit the ability of the human hormone to react to antiserum raised against the mouse hormone. Antiserum to mouse β-endorphin was prepared as described by Allen, et al., *Proc. Nat'l. Acad. Sci.* 75, 4972 (1978). Human β-endorphin was synthesized by the solid phase technique as described by Li, et al. supra, and was radioactively labeled with $^{125}I$ by a chloramine-T procedure (Hunter, H. M. and Greenwood, J. C. *Native*, 194, 495(1962). The iodinated peptide was purified by adsorption to 35 mg glass powder in 10 ml of buffer (pH 7.4) containing 0.05 M sodium phosphate, 0.25% human albumin and 0.5% β-mercaptoethanol. After mixing for 5 min., the suspension was spun at 3500 rpm for 5 min. washed once with 5 ml water and then eluted with 2 ml of 40% (v/v) acetone in 0.25 HCl.

In the assay, a dilution series of β-endorphin sample prepared according to the present invention was incubated with a fixed amount of labeled human endorphin and a fixed amount of antiserum. Reaction mixtures contained 75 μl of $^{125}I$-human β-endorphin (10,000) cpm), 50 μl of protein solution prepared as described in Example 4 from either pβgal-containing bacteria or from pβgal-end containing bacteria, in 0.05 M sodium phosphate pH 7.4, 0.25% (w/v) human albumin and 0.5% β-mercaptoethanol. Antiserum was added to a final volume in the reaction mixture of 150 μl. Incubations were carried out at 4° C. for 24 hours. Antigen-antibody complexes were separated from the reaction mixture by adsorption to a dextran-charcoal suspension containing 3% (w/v) charcoal (Norit A, Pfanstiehl Chemical Company, Waukegan, Ill.), 0.75% (w/v) dextran (Schwartz-Mann, Van Nuys, Calif.) and 60% (w/v) horse serum (Grand Island Biological Company, Santa Clara, Calif.) in 0.5 M sodium phosphate pH 7.6.

The suspension was incubated for 5 minutes at 4° C., then centrifuged at 2,500 rpm for 15 minutes. The supernatant containing bound antigen was aspirated with a glass bent-tip pipette. The percentage of radioactivity remaining in the pellet was compared to the total radioactivity determined prior to incubation and plotted as a function of the concentration of the cell extracts. The results are shown in FIG. 5.

Figure 5:
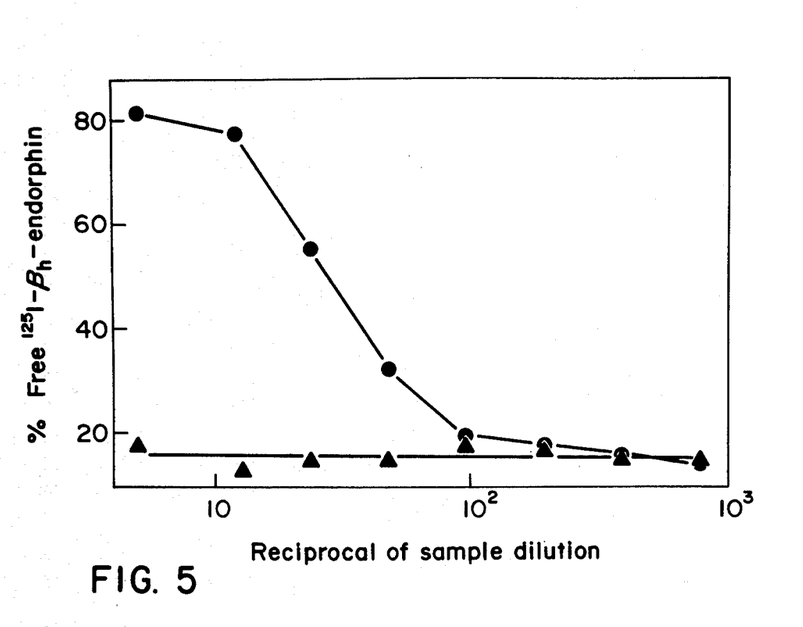

It is apparent from FIG. 5 that extracts derived from cells bearing plasmid pβgal-end (solid circles) competed with labeled human β-endorphin for the available antibody. In a control experiment, extracts from cells carrying the plasmid pβgal (triangles) had no competitive effect. The coefficients of variation in these experiments were less than 5%.

EXAMPLE 6

Receptor Binding Activity

In the following experiment, the ability of β-endorphin, made according to the present invention, to competitively inhibit the binding of a radioactively labeled opiate agonist or a labeled antagonist for the binding to rat brain opiate receptors was tested. The opiate receptor preparation was prepared from rat membrane preparations isolated from male Sprague-Dawley rats (200–220 g) killed by decapitation. The brains, except for the cerebellum, were homogenized in 40 volumes of ice-cold Tris-HCl buffer pH 7.7. The homogenates were centrifuged at 600 g for 5 minutes, then the supernatant fluid was centrifuged at 49,000 g at 4° C. for 15 minutes. The pellets were re-suspended in 5 ml at 0.05 M Tris-HCl buffer pH 7.7 and incubated at 37° C. for 30 minutes, then centrifuged at 49,000 g at 4° C. for another 15 minutes. The final pellet from each rat brain was then re-suspended in 40 ml of 0.05 M Tris-HCl buffer pH 7.7 containing 100 μg/ml of Bacitracin and used for the binding assays.

The binding experiments were performed either at 25° C. for 20 minutes or at 0° C. for 3 hours. The reaction mixtures contained 1 ml of the rat membrane preparation as described, 1.5 nM of $^3H$-methionine enkephalinamide (38 Ci/m Mole) or $^3H$-naloxone (25 Ci/m Mole) together with bacterial extracts from pβgal or pβgal-end transformed cultures. (4.5 mg protein for enkephalinamide reactions and 0.65 μg protein for naloxone reactions). At the end of the binding reaction the mixture was filtered under vacuum over glass fiber filters (Whatman, Clifton, N.J., GH-B filters). The filters were washed with a large volume of cold. 0.05 M Tris buffer pH 7.7 and placed in scintillation vials containing 12 ml of Hydromix (TM Yorktown Research, South Hackensack, N.J.) scintillation fluid and placed in a scintillation counter to determine the amount of radioactive agonist or antagonist bound. The results are shown in the following Table 1:

| | | E. coli RR1 Radioligand | | | |
|---|---|---|---|---|---|
| | | $^3H$—ala-enkephalinamide (agonist) | | $^3H$—naloxone (antagonist) | |
| Plasmid | Source | μg protein | % inhibition | μg protein | % inhibition |
| pβgal-end | pellet | 5, 10 | 84, 100 | 0.7 | 68 |
| pβgal | pellet | 4 | 65 | 0.6 | 25 |

It can be seen that β-endorphin from the cell pellet fraction of bacteria transformed with pβgal-end is an effective inhibitor of the binding of both an agonist and an antagonist to opiate receptors of the brain. The displacement of both the opiate agonist enkephalinamide and the opiate antagonist naloxone was greater in material obtained from the cell pellet fraction after sonication than in the total bacterial cell extract.

EXAMPLE 7

The Effects of β-Endorpin on Prostaglandin E₁-Stimulated Adenyl Cyclase Activity in Neuroblastoma-Glioma Hybrid Cells The neuroblastoma-glioma hybrid cell line NG 108-15 is richly endowed with opiate receptors and possesses an adenylate cyclase which can be stimulated by prostaglandin E₁ (Klee, W. and Nivenberg, M. *Proc. Natl. Acad. Sci.*, 71, 3474 (1974); Hamprecht, B. and Schultz, J. Happe-Selyers Z. Physiol. Chem., 354, 1633 (1973)). This stimulation is inhibited by morphine and the inhibitory affect of morphine can be prevented by naloxone, a morphine antagonist (Trober, J. et al., *Nature*, 253, 120 (1975)). The β-endorphin preparation used in these experiments was obtained from fully-induced cells transformed either with pβgal or pβgal-end, using the pellet fraction obtained after sonication, as described in Example 3, without further purification by adsorption to glass. The neuroblastoma-glioma hybrid cells were grown in T-flasks (1 flask for 60 assays) in Dulbecco's modified Eagle's medium (Dulbecco, R., *Virology* 8, 369 (1959)) containing 10% (v/v) fetal calf serum, 0.1 mM hypoxanthine, μM aminopterin and 16 μM thymidine. At confluency, cells were harvested and homogenized in 0.32 M sucrose, 40 mM HEPES and 2 mM EDTA, pH 7.6.

The test reaction measured the amount of cyclic AMP synthesized by the cultured cells in the presence of prostaglandin E₁ measured in the presence and absence of β-endorphin prepared according to the invention as described in Example 3 (without purification by glass extraction). The base line level of adenylate cyclase stimulated by prostaglandin E₁ was determined in the absence of any opiate agonist or antagonist. Inhibition of the stimulated adenylate cyclase level was observed when the incubation was carried out in the presence of a known opiate agonist or in the presence of an extract of cell sonicate pellet material prepared from fully induced *E. coli* RR1 bearing the pβgal-end plasmid and treated as described above to releave the β-endorphin. Further, the ability of naloxone, an opiate antagonist, to reverse the effect of β-endorphin was tested. As a control, the test was run using a similarly-treated sonicate pellet of fully induced *E. coli* RR1 bearing pβgal. The incubations were carried out for 15 minutes at 30° C. in a total reaction volume of 100 μl containing ³²P-ATP, 3×10⁶ cpm, 10 units creatine phosphokinase, 50 μM prostaglandin E, 5 μl of opiate agonist or pellet extract (3.5 μg protein) as described in Example 3, 20 mM HEPES, 5 mM MgCl₂, 1 mM cAMP, 20 mM creatine phosphate, 0.1 mM ATP, 0.125 mM ZK 62711, a phosphodiesterase inhibitor (Schilling, West Germany), and 1 mM of protease inhibitor (Sigma Chem. Co.). At the end of the incubation period, the reaction was stopped by the addition of 150 μl of 1 N HClO₄, following which 0.3 ml of water containing 30,000 cpm of tritiated cyclic AMP was added per tube as a marker. The tube contents were mixed and centrifuged, following which the supernatant solution was fractionated by column chromatography by Dowex 50 (TM Dow Chemical Company, Midland, Mich.) and alumina to recover ³²P-cAMP synthesized in the reaction (White, A. A., and Kan D. B., *Anal. Biochem*, 85, 451 (1978). The amount of cAMP synthesized, from which the adenylate cyclase activity was inferred, was measured by quantitative determination of the ³²P counts. The results, expressed as percent inhibition of the prostaglandin E₁ stimulated activity measured in the absence of added optiate agonist, are shown in the following β-endorphin, prepared from the cell sonicate pellet of bacteria transformed by pβgal-end inhibited the adenylate cyclase activity, and the inhibition was reversed by the addition of naloxone. By contrast, the cell pellet fraction derived from bacteria transformed by pβgal did not significantly inhibit the base line adenylate cyclase activity.

TABLE 2:

| Plasmid | μg Protein | Inhibition (%) – Naloxone | + Naloxone |
|---------|-----------|---------------------------|------------|
| pβgal-end | 3.5 | 23 | 0 |
| pβgal | 3.0 | 5 | 0 |

EXAMPLE 8

Synthesis of Human β-Endorphin

The principles of the present invention are applied in combination with prior art techniques to provide a modified coding sequence whose expression yields human β-endorphin. The method takes advantage of the fact that the coding sequence for mouse '-endorphin contains a HhaI site (GCGC) spanning amino acids 26 and 27 of the mouse β-endorphin sequence. A sequence coding for human β-endorphin may be constructed by cleaving the mouse sequence with HhaI endonuclease, followed by ligation of the chemically synthesized nucleotide sequence coding for the 5 C-terminal amino acids of human β-endorphin.

The mouse coding sequence, prepared as described in Example 1 through the S₁ nuclease digestion step, is treated with 5 units of HhaI endonuclease for 1 hour at 37° C. in the manufacturer's recommended reaction buffer. The DNA is separated from a reaction mixture by phenol extraction and ethanol precipitation, as described in Example 1. The DNA is then joined to a synthetic oligonucleotide having the structure The synthetic oligonucleotide is synthesized chemically as described by Itakura, K., et al., *J. Am. Chem. Soc.* 97, 7327 (1975). Alternatively, the oligonucleotide is obtained by commercial custom synthesis from Collaborative Research, Inc., Waltham, Mass. The joining reaction is catalyzed by T 4 DNA ligase as described in Example 1 using a 20-fold molar excess of the oligonucleotide and 1/10 the amount of DNA ligase, in an incubation at 14° C. overnight. Joining of the synthetic oligonucleotide to the HhaI-treated endorphin coding fragment is facilitated by the two unpaired nucleotides resulting from the asymmetric cleavage by HhaI endonuclease. Joining of the oligonucleotide to the endorphin coding fragment in reverse orientation is therefore prevented while blunt end ligation of the synthetic oligonucleotide to the opposite end of the endorphin coding fragment is minimized by the choice of reaction conditions. In the event such mistaken joining occurs, the resulting unpaired end insures that the reaction product cannot find its way into a plasmid. The ligase reaction product is now identical in sequence to the product resulting from S1 nuclease action in Example 1 except that the C at the beginning of the histidine codon of the mouse endorphin sequence is replaced by a T, thereby providing a tyrosine codon for amino acid 27 and the C at the beginning of the glutamine codon is replaced by a G, thereby providing a glutamic acid codon for amino acid 31. The coding fragment now codes for human β-endorphin. The human β-endorphin coding fragment is further treated as described in Example 1 by the addition of EcoR1 linkers, treatment with EcoR1 endonuclease and insertion into the EcoR1 site of plasmid pβgal. Bacterial cells transformed with pβgal-end (human) synthesized the human β-endorphin as a fusion protein joined to β-galactosidase. Treatment of the fusion protein as described in Examples 2, 3 and 4 results in purified human β-endorphin, synthesized by a bacteria bearing a transfer vector comprising a mammalian coding sequence.

Alternatively, the starting materials for the above modification procedure may be the plasmid pβgal-end treated with EcoR1 endonuclease to release the endorphin coding fragment. The latter is then separated from the plasmid by gel electrophoresis, then cleaved with HhaI endonuclease as described. The synthetic oligonucleotide to be joined may have the same sequence as described, or may in the alternative contain additionally the octanucleotide R1 linker sequence on its blunt end. Use of the alternative synthetic oligonucleotide obviates the need for a separate blunt end ligation of R1 linker octamers, since the insert released from pβgal already bears an R1 site sequence. Similar synthetic inserts may be used to provide coding sequences for the expression of the "super-agonist" endorphins described by Li, C. H., supra., including Gly$^{31}$-endorphin, Gly$^{31}$-endorphinamide and Gly$^{31}$-endorphinyl-glycine.

EXAMPLE 9

In Vitro Synthesis of β-Endorphin

The expression of the β-endorphin coding region is carried out in vitro using the DNA-directed protein synthesis system described by Zubay, G., *Ann. Rev. Genetics* 7, 267 (1973). The DNA used in the synthesis is either the recombinant plasmid pβgal-end or the modified recombinant plasmid described in Example 8 for expression of human β-endorphin. In addition, restriction endonuclease cut fragments of the described plasmids, including the β-endorphin coding region, may be employed in the Zubay system. One or more of the amino acids provided in the system is radioactively labeled, in order to permit a sensitive assay for the product protein. Synthesis of β-endorphin is detected by the binding of radioactively labeled material to antiβ-endorphin antibody or in any of the assay systems previously described. Where one of the described expression plasmids is used to direct synthesis, a fusion protein is synthesized. The fusion protein is modified to provide true β-endorphin, as described in Examples 3 and 4.

Similar manipulations and modifications may be made following the principles of the present invention, alone or in combination with prior art techniques, to synthesize modified peptides having modified endorphin-like activity, modified species specificity or improved bio-availability.

While the invention has been described in connection with specific embodiments thereof, it will be understood that it is capable of further modifications, and this application is intended to cover any variations, uses, or adaptations of the invention following, in general, the principles of the invention and including such departures from the present disclosure as come within known and customary practice within the arts to which the invention pertains and as may be applied to the essential features herein before set forth, and as follows in the scope of the appended claims.

We claim:

1. A method of making a peptide having opiate agonist or antagonist activity comprising the steps of:
    (a) providing a cloned mammalian DNA fragment comprising a naturally occurring mammalian codon sequence, coding for said peptide,
    (b) providing a stop condon selected from the group consisting of TGA, TAA and TAG, said stop codon being in phase with said coding sequence adjacent to and in reading frame phase with a codon for a COOH-terminal amino acid of said peptide,
    (c) inserting said coding sequence into an internal position in an expressible bacterial gene in a DNA transfer vector, such that the cloned mammalian coding sequence is followed by said stop codon and is in the same orientation with respect to translation as the bacterial gene, such that readthrough translation of the inserted coding sequence can take place resulting in a fusion protein comprising said peptide, said peptide being joined to the remainder of said fusion protein by an arginine residue,
    (d) protecting said fusion protein with a reagent capable of reacting with lysine epsilon amino groups in order to prevent trypsin action at the site of said lysine residues,
    (e) digesting the fusion protein with trypsin, and
    (f) deprotecting the lysine residues thereby yielding a peptide having opiate agonist or antagonist activity.

2. The method of claim 1 wherein the cloned mammalian DNA fragment comprising a naturally occurring mammalian codon sequence comprises additionally a synthetic DNA sequence such that the expression product protein is modified.

3. A method according to claim 1 wherein the lysine residues are protected by reaction with citraconic anhydride.

4. A DNA transfer vector having an expressible bacterial gene and having inserted therein a nucleotide sequence comprising codons coding for a peptide having opiate agonist or antagonist activity, said nucleotide sequence comprising a naturally-occurring mammalian sequence coding for said peptide and being followed by a stop codon selected from the group consisting of TGA, TAA and TAG, said stop codon being in phase with said coding sequence and being adjacent to and in reading frame phase with a codon coding for a COOH-terminal amino acid of said peptide, said nucleotide sequence being inserted in such orientation with respect to said bacterial gene that expression of said gene results in synthesis of a protein comprising said peptide.

5. The transfer vector of claim 4 comprising a plasmid comprising the lac operon.

6. The transfer vector of claim 5 wherein the inserted nucleotide sequence codes for mouse β-endorphin.

7. The transfer vector of claim 5 wherein the inserted nucleotide sequence codes is human β-endorphin.

8. The transfer vector of claim 4 wherein the inserted nucleotide sequence comprises additionally a synthetic oligonucleotide sequence such that said nucleotide sequence codes for a peptide selected from the group consisting of: mouse β-endorphin, human β-endorphin, Gly$^{31}$-human β-endorphin, and Gly$^{31}$-human β-endorphinyl glycine.

9. A microorganism containing, replicating and expressing the transfer vector of any of claims 4, 5, 6, 7 or 8.

10. A microorganism according to claim 4 containing, replicating and expressing the transfer vector pβgal-end.

11. The microorganism of claim 10 comprising the bacterial strain *E. coli* RR1.

* * * * *